United States Patent [19]

Gordon

[11] Patent Number: 4,534,963
[45] Date of Patent: Aug. 13, 1985

[54] HIGH PEARLESCENT PRESSED POWDER EYE SHADOW COMPOSITION

[75] Inventor: Philip J. Gordon, Southbury, Conn.

[73] Assignee: Chesebrough-Pond's Inc., Greenwich, Conn.

[21] Appl. No.: 515,943

[22] Filed: Jul. 20, 1983

[51] Int. Cl.$^3$ .................... A61K 7/035; A61K 7/021; A61K 47/00
[52] U.S. Cl. ........................ 424/69; 424/63; 424/358; 514/785
[58] Field of Search .................... 424/63, 64, 69, 358, 424/365

[56] References Cited

U.S. PATENT DOCUMENTS

| | | |
|---|---|---|
| 2,937,129 | 5/1960 | Garwood . |
| 3,196,079 | 7/1965 | Blaustein .................. 424/63 |
| 3,475,369 | 10/1969 | Blunt ...................... 424/69 |
| 3,978,207 | 8/1976 | Fotiu et al. . |
| 4,322,400 | 3/1982 | Yuhas . |
| 4,343,863 | 8/1982 | Lawrence et al. . |
| 4,371,398 | 2/1983 | Forchielli . |

FOREIGN PATENT DOCUMENTS

| | | |
|---|---|---|
| 0005922 | 12/1979 | European Pat. Off. ............ 424/64 |
| 4355 | 1/1980 | Japan .................... 424/69 |
| 34610 | 4/1981 | Japan .................... 424/69 |

OTHER PUBLICATIONS

Bareco Product Data Sheet Release No. 500.3—2 pages.
Bareco Product Literature re Vybar ® Polymers.
Bareco Product Data Sheet Release No. 100.2—2 pages.
Liponate Product Literature No. 680T re Liponate PO-4.
"Eyeshadows—Pressed Tablets", *The Chemistry and Manufacture of Cosmetics*, vol. IV, 2nd Edition, pp. 719-725.
"Eye Makeup" by Julius Wetterhahn, *Cosmetic Science and Technology*, vol. I, 2nd Edition, Chapter 13, pp. 393-407.
Chemical Abstracts, vol. 93, No. 26, Dec. 1980, p. 374, No. 245273q.

*Primary Examiner*—Sidney Marantz
*Assistant Examiner*—Shawn P. Foley
*Attorney, Agent, or Firm*—Brumbaugh, Graves, Donohue & Raymond

[57] ABSTRACT

A pressed powder cosmetic eye shadow composition containing from about 40–80% by weight of nacreous material and a binder comprising a dry binder ingredient selected from the group consisting of cosmetically suitable micronized polyethylene wax and a mixture of liquid/solid binder ingredients comprising petrolatum; a cosmetically suitable tetraester having the formula

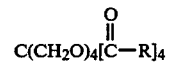

wherein R may be a straight, branched, saturated or unsaturated alkyl having from 5 to 21 carbon atoms; and a cosmetically suitable polyolefin (synthetic wax) formed by polymerizing an alpha olefin having the formula $RCH{=}CH_2$, wherein R is a hydrocarbon group having from 3 to 18 carbon atoms.

25 Claims, No Drawings

HIGH PEARLESCENT PRESSED POWDER EYE SHADOW COMPOSITION

BACKGROUND OF THE INVENTION

This invention relates to cosmetic eye shadow compositions and specifically pearlescent, pressed powder eye shadow compositions and to a process for their preparation.

Pressed powder eye shadow compositions containing nacreous pigments such as natural pearl, mica, bismuth oxychloride, bismuth oxychloride on mica, titanated mica, and titanated mica and iron oxide, are well-known in the cosmetic industry and widely used by consumers to highlight the eyes by imparting an iridescent effect to the eyelid area. Said compositions are generally manufactured by compacting a powder composition under pressure in suitable recepticles to form a cake or tablet. The finished product is generally applied to the eyelid area with a foam tipped applicator or soft brush. Pressed powder eye shadow compositions which contain high levels of pearlescent material are generally preferred since these compositions impart to the eyelids the most dramatic iridescent affects.

However, it has been found that pressed powder eye shadow formulations having a high pearlescent content give rise to a number of serious manufacturing problems foremost of which is the problem of achieving satisfactory compactibility of the composition. Acceptable compaction of pressed powder eye shadow compositions is a function of the amount of pearlescent material, the binder system used in compounding the composition, the size of the recepticle into which the composition is compacted, the pressure under which the composition is compacted and the speed at which the composition is compacted, i.e. the number of units compacted per minute.

To begin with, pressed powder compositions which contain less than about 40% by weight of pearlescent materials generally exhibit unacceptable reflectivity on the skin and for that reason are not considered a pearlescent eye shadow. It has been found that suitable skin reflectivity is only realized where the eye shadow compositions contain 40% or more pearlescent material. However, such compositions are difficult to compact and often exhibit poor skin adhesion properties. While various binder systems have been employed to aid in overcoming compaction problems, the high pearlescent formulations have a tendency to produce softer pressed cakes which often fail to meet standard industry drop tests and ship tests and therefore, lead to a high rejection rate at the pressing operation or consumer dissatisfaction because of glazing or crumbling tendancies. While the specific binder system used in the pressed powder high pearlescent formulations is critical to successful compaction, pressability of a formulation is also dependent on the dimensions of the pans or godets into which the formulations are pressed and the speed at which the pressing operation is carried out. Currently, those manufacturing high pearlescent compositions are constrained to use small circular or rectangular shaped pans (approximately 1″ in diameter, length or width and approximately ⅛″ in depth) when pressing at high speed. If the pan size is substantially larger, it is generally necessary to reduce the pressing speed in order to achieve satisfactory. Obviously, this pan size/pressing speed dilemma contributes to the cost of manufacture.

As a result of the present invention, the aforementioned problems encountered in the manufacture of pearlescent pressed powder eye shadow compositions have been eliminated altogether or significantly reduced.

SUMMARY OF THE INVENTION

Hence, it is an object of the present invention to provide pressed powder eye shadow compositions which contain high concentrations of pearlescent material such as natural pearl, mica, bismuth oxychloride, bismuth oxychloride on mica, titanated mica, and titanated mica and iron oxide and which are easily compacted.

It is another object of the present invention to provide a binder system for pearlescent materials which permit the use of less costly pearlescent material without diminishing the high luster associated with more costly pearlescent materials.

It is another object of the present invention to provide pressed powder eye shadow compositions which have excellent skin application, adhesion, and wearability properties.

It is a further object of the present invention to provide high pearlescent, pressed powder eye shadow compositions which can be compacted at high speeds.

It is a further object of the present invention to provide high pearlescent, pressed powder eye shadow compositions which can be pressed in pans having a wide variety of dimensions and shapes, particularly pans having large dimensions.

It is a further object of the present invention to provide high pearlescent, pressed powder eye shadow compositions which can consistently meet and surpass standard industry drop tests and shipping tests.

Yet another object of the present invention is to provide a process for obtaining high pearlescent pressed powder eye shadow compositions which possess the foregoing characteristics.

These, as well as other objects of the present invention, will become apparent from the following disclosure.

In accordance with the present invention, it has been found that the addition to particles of mica, as well as other suitable pearlescent materials, of the novel binder system described hereinbelow, provides pressed powder eye shadow compositions which permit the utilization of high concentration of pearlescent material, which can be compacted at high pressing speeds into recepticles having a wide variety of shapes and sizes and which exhibit all of the desired properties of an excellent pressed powder eye shadow.

The nacreous or pearlescent materials that may be used in accordance with the present invention include all conventional materials used to effect iridescence. Typical pearlescent materials include nacreous pigments such as natural pearl, mica, bismuth oxychloride, bismuth oxychloride on mica, titanated mica, and titanated mica and iron oxide. However, the novel binder system now affords the opportunity of utilizing lower cost pearlescent material without the usual concomitant loss in pearlescence, since the binder, in addition to the primary compaction role which it plays, imparts an enhanced luster, gloss or iridescence to the pearlescent material.

In accordance with the present invention, the novel eye shadow compositions contain from about 40% to 80% by weight of pearlescent material, with the preferred range of said materials being from about 45% to 70% by weight.

The novel binder system employed in the present invention is a two-part system comprising a dry powdered binder ingredient which is mixed with the pearlizing agent or agents along with other optional, conventional dry (powdered) eye shadow ingredients, e.g. talc, metal soaps, colorants, fragrances and preservatives, and a liquid binder mixture comprising suitable moisturizers, emollients and lubricants.

The dry binder ingredient is a cosmetically suitable micronized polyethylene wax, i.e. a highly crystalline polymer having a molecular weight range, from about 600 to 4000 and preferrably from about 700 to 800 and a particle size from about 2 microns to 35 microns which facilitates incorporation of said binder with the other powdered ingredients to produce a homogeneous mixture quickly and efficiently. The preferred dry binder ingredient and its properties is set forth in Table I below:

TABLE I

| MICRONIZED POLYETHYLENE WAX | |
|---|---|
| Particle Size | 25 microns Avg. |
| Molecular Weight | 750 |

It has been found that a crystalline micronized polyethylene wax manufactured by the Bareco Division of Petrolite Corporation is preferred. SILTEK M, the trade name of this micronized polyethylene wax has the properties set forth in Table II.

TABLE II

| SILTEK M | |
|---|---|
| Melting point | 219° F. (104° C.) |
| Particle size | 25 μAvg. |
| Molecular weight | 750 |
| Density 77° F. (25° C.) | 0.96 grs/cc |
| Viscosity 300° F. (99° C.) | 50 SUS |

When used in conjunction with the liquid phase of the binder system, it has been found that micronized polyethylene wax is capable of binding difficult systems containing up to 80% pearlescent pigments, e.g. titanated mica, without glazing or cake agglomeration. The effectiveness of micronized polyethylene wax is in part attributed to the cold-flow properties which it possesses. The amount of dry binder ingredient used in the present invention ranges from about 0.1% to 15% by weight, with the preferred amount ranging from about 0.5% to 9.0% by weight.

The liquid phase of the binder system comprises the following ingredients: petroleum jelly (petrolatum), a tetraester having the general formula

wherein R may be a straight, branched, saturated or unsaturated alkyl group having from 5 to 21 carbon atoms; and a polyolefin formed by polymerizing an alpha-olefin having the general formula $RCH=CH_2$, wherein R is a hydrocarbon group having from 3 to 18 carbon atoms.

Petroleum jelly or petrolatum is a purified mixture of semi-solid hydrocarbons from petroleum, chiefly the methane fraction having a general formual $C_nH_{2n+2}$. More specifically, petrolatum is a collodial system of non-straight chain solid hydrocarbons and high boiling liquid hydrocarbons in which most of the liquid hydrocarbons are held inside the micelles. Petroleum is utilized to aid in binding the various powdered ingredients in the eye shadow composition as well as to provide moisturization. Moreover, it has been found that the use of petrolatum improves the wear in pressed powder eye shadows and imparts a water-resistant property to said cosmetic compositions. The amount of petroleum jelly present in the liquid phase of the binder system ranges from about 0.25% to 5.5% by weight, with the preferred range being from about 0.75% to 3.5% by weight.

The tetraester ingredient present in the liquid phase of the binder system is a tetraester of pentaerythritol and a cosmetically suitable acid, e.g. lauric, oleic, stearic, palmitic, linoleic, isostearic, hydroxystearic, acetic and a branched chain nonanoic acid. The tetraester of pentaerythritol and oleic acid and particularly the product sold under the trade name LIPONATE PO-4 manufactured by LIPO Chemical Inc. is a preferred binder ingredient. It has been found that the use of LIPONATE PO-4 not only imparts exceptional lubricity but also improves the luster of the pearlescent materials used in the eye shadow formulations. The amount of the tetraester ingredient in the present invention ranges from about 1.0% to 15% by weight, with the preferred range being from about 2.0% to 4.5%.

The polyolefin (synthetic wax) component of the liquid phase of the binder system and the process for making the same is disclosed, inter alia, the U.S. Pat. No. 2,937,129. Hexene-1, heptene-1, octene-1, decene-1, undecene-1, dodecene-1 and tetradecene-1, are examples of typically polyolefins suitable for use in the present invention. However, dodecene-1, and specifically that compound sold under the trademark VYBAR ®825, manufactured by the Bareco Division of the Petrolite Corporation, is preferred. The polyolefin component functions as a lubricant which not only aids in binding the powder ingredients but also serves as an inorganic pigment (iron oxide) wetting agent and enhances color, intensity and wearability of the final eye shadow compositions. The amount of the polyolefin in the present invention ranges from about 0.1% to 3.0% by weight, with the preferred amount ranging from about 0.5% to 2.0% by weight.

While the foregoing describes the essential ingredients of the two-part binder system which is incorporated with the pearlizing agent, other optional ingredients may be added to either the pearlescent material or the binder system. For example, talc, i.e. the transparent forms thereof, is often used as a filler in conjunction with the pearlescent material in a pressed powder eye shadow composition. In the preferred embodiments of the present invention, talc may be present in amounts up to about 40% by weight.

Cosmetically suitable metal soaps, such as metallic stearates, e.g. zinc, lithium, magnesium and calcium stearates, are utilized in powder form to impart good skin adhesion and lubricity to the eye shadow composition. In preferred embodiments of the present invention, zinc stearate may be present in amounts up to about 6.0% by weight.

Additional optional ingredients include effective amounts of conventional, cosmetically suitable preservatives, colorants, such as ironoxide pigments as well as natural pigments, and fragrances. As with all ingredients in the eye shadow compositions of the present invention, it is important, due to the great sensitivity of the eye area, to avoid using any ingredients which could act as an irritant and the use of the phrase "cosmetically suitable" as used herein is intended to mean that the particular ingredient is pure, safe, non-toxic and non-irritating.

Optional ingredients which may be incorporated into the liquid phase of the two-part binder system include fatty esters and triesters of glycerine and a cosmetically suitable acid.

The fatty esters contemplated for use in the present invention are characterized by the general formula

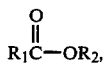

wherein $R_1$ is a group containing from 1 to 21 carbon atoms which may be straight or branched, saturated or unsaturated and which may contain hydroxyl groups; $R_2$ is a group containing from 1 to 22 carbon atoms which also may be straight or branched, saturated or unsaturated and which may contain hydroxyl groups; and further wherein $R_1$ and $R_2$ may be the same or different; or having the general formula

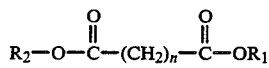

wherein "n" is an integer from 2 to 6 and $R_1$ and $R_2$ have the same meanings as disclosed above and may be the same or different. In a preferred embodiment of the present invention, octyl palmitate and particularly that compound sold under the trade name of Ceraphyl 368, manufactured by VanDyk & Company, Inc. is used. Other suitable fatty esters include isopropyl, palmitate, isostearyl neopentanoate, isopropyl lanolate, isopropyl myristate. Those skilled in the art will be aware of the fatty esters that are available. The fatty ester ingredient may be present in the eye shadow composition in amounts up to about 15% by weight, with the preferred range being from about 1.5% to 5.5% by weight. The fatty ester primarily serves as a wetting agent for the pearlescent pigment and improves the high pearlescent cake appearance, product application and powder pressability.

In addition to the optional fatty ester ingredient, the liquid binder phase may also (optionally) include triesters of glycerin and a cosmetically suitable acid selected from the group consisting of lauric, stearic, oleic, palmitic linoleic, isostearic, hydroxystearic, acetic and branched chain nonanoic acids, e.g. respectively, trilaurin, tristearin, triolein, tripalmitin, trilinolein, triisostearin, trihydroxystearin, triacetin and triisononanoin. Said triesters are primarily used as emollients in pressed powder eye shadow compositions of the present invention and have been found to improve the wear and to impart a water-resistance to said compositions. A suitable triester or mixture of triesters, i.e. selected from those disclosed herein may be present in the novel cosmetic formulations in an amount up to about 7.0% by weight, with preferred amount ranging from about 0.4% to about 5.5% by weight. Of the aforementioned triesters, trilaurin is preferred and specifically the compound sold under the trade name SOFTISAN 100, manufactured by K-Fries Inc., Division of Dynamit Nobel.

It will be obvious to those skilled in the art that other optional ingredients may also be incorporated in the novel cosmetic formulations of the present invention, for example antioxidants and water, hence the examples of optional ingredients heretofore described are not intended to be limiting in any respect.

In preparing the pressed powder eye shadow compositions of the present invention the powdered (dry) ingredients, discussed supra, are individually weighed and placed in a twin-cone blender, and dry blended for approximately two minutes to produce a uniform, homogenous mixture.

The liquid and solid binder ingredients are individually weighed, placed in a vessel and liquified by heating to approximately 190° F. The liquified mixture is then sprayed under pressure into the blender containing the dry mixed ingredients with agitation to produce a homogenous bulk, powdered eye shadow formulation.

The bulk, powdered eye shadow formulation is then transferred to the hopper of a standard pressing apparatus, for example an Arenco Press and gravity fed to a cavity, the bottom of which contains the godet (pan). A pressing ribbon is fed over the filled cavity and the powdered formulation is compacted into the godet by means of a punch at a pressure of about 1200 to about 9000 psi for approximately two seconds. Thereafter, the godet is ejected from the cavity and replaced by an empty godet and the process is repeated. Those skilled in the art will be fully familiar with the above-described press apparatus and its operation.

The invention will be more fully understood from the examples which follow, which are presented herein by way of illustration and are not to be considered as limiting.

EXAMPLE 1

Seventy pounds of an eye shadow formulation MPG-02-24A Batch 240D (Blue), were prepared in accordance with the procedure disclosed hereinabove. Said formulation contained the following percents by weight of ingredients:

| Dry Ingredients | | Liquid/Solid Ingredients | |
|---|---|---|---|
| 40.95 | Titanated Mica | 4.30 | Ceraphyl 368 |
| 18.00 | Mica | 3.57 | Liponate PO-4 |
| 10.00 | Bismuth Oxychloride | 2.90 | Softisan 100 ® |
| 6.00 | Talc | 2.80 | Petroleum Jelly |
| 6.00 | Zinc Stearate | 1.43 | VYBAR ® 825 |
| 2.50 | SILTEK M | 15.00 | |
| 1.10 | Colorants | | |
| 0.20 | Germall 115 | | |
| 0.15 | Methylparaben | | |
| 0.10 | Propylparaben | | |
| 85.00 | | | |

Packers of pressed samples (575 pieces each) were prepared on a "Arenco", Model AT8 powder press fitted with a double (2) cavity die station. Each sample was pressed at 3769 psi into godets having the dimensions 0.956″×0.806″×0.112″ at a pressing speed of 48 pieces per minute.

EXAMPLE 2

Two hundred and twenty-five pounds of an eye shadow formulation MPG-02-146 Batch 310C (Rose) was prepared using the identical procedure as was used in preparing the formulation of Example 1; however, the percent by weight of SILTEK M was increased from 2.5% to 3.75% and the godet size was also increased.

Samples of the present formulation were pressed using the identical apparatus used in Example 1 except for a powder press change over from double to single cavity die station in order to accommodate the size of the larger godet.

Samples (Packers of 260 pieces each) were pressed at 2630 psi into godets having the dimensions of 2.435"×0.950"×0.120" at a pressing speed of 21 pieces per minute.

EXAMPLE 3

Two hundred and twenty-five pounds of an eye shadow formulation MPG-02-150 Batch 309A (Cream) were prepared using the identical procedure as was used in preparing the formulation of Example 1; however, the percent by weight of SILTEK M was increased to 5.0%.

Pressing parameters were essentially the same as those used in Example 2; however, each sample was pressed at 2630 psi into godets having the same configuration and dimensions of the godets used in Example 2. The pressing speed was approximately 21 pieces per minute.

EXAMPLE 4

Two hundred and twenty-five pounds of an eye shadow formulation MPG-02-144 Batch 310A (Dark Blue) were prepared using the identical procedure as was used in preparing the formulation of Example 2.

Pressing parameters were essentially the same as those used in Example 2; however, each sample was pressed at 2958 psi into godets having the same configuration and dimensions of the godets used in Example 2. The pressing speed was approximately 21 pieces per minute.

EXAMPLE 5

Two hundred and twenty-five pounds of an eye shadow formulation MPG-03-6 Batch 319A (Dark Blue) were prepared using the identical procedure as used in preparing the formulation of Example 4; however, the percent by weight of SILTEK M was increased from 3.75% to 5.0%.

Pressing parameters were essentially the same as those used in Example 2; however, each sample was pressed at 2465 psi into godets having the same configuration and dimensions of the godets used in Example 2. The pressing speed was approximately 24 pieces per minute.

EXAMPLE 6

Two hundred and twenty-five pounds of an eye shadow formulation MPG-02-148 Batch 310A (Light Blue) were prepared using the identical procedure as was used in preparing the formulation of Example 3.

Pressing parameters were essentially the same as those used in Example 2; however, each sample was pressed at 2630 psi into godets having the same configuration and dimensions of the godets used in Example 2. The pressing speed was approximately 21 pieces per minute.

EXAMPLE 7

Two hundred and twenty-five pounds of an eye shadow formulation MPG-03-8 Batch 316A (Light Blue) were prepared using the identical procedure as was used in preparing the formulation of Example 6; however, the percent by weight of SILTEK M was increased from 5.0% to 7.5%.

Pressing parameters were essentially the same as those used in Example 2; however, each sample was pressed at 2465 psi into godets having the same configuration and dimensions of the godets used in Example 2. The pressing speed was approximately 22 pieces per minute.

EXAMPLE 8

An eight pound laboratory batch of an eye shadow formulation MPG-03-80 (Light Brown) was prepared in a laboratory twin-cone blender using the identical procedure as was used in preparing the formulation of Example 1. Said formulation contained the following percents by weight of ingredients:

| Dry Ingredients | | Liquid/Solid Ingredients | |
| --- | --- | --- | --- |
| 20.00 | Titanated Mica | 4.30 | Ceraphyl 368 |
| 20.00 | Mica | 3.57 | Liponate PO-4 |
| 6.00 | Talc | 2.90 | Softisan 100 ® |
| 6.00 | Zinc Stearate | 2.80 | Petroleum Jelly |
| 5.00 | SILTEK M | 1.45 | VYBAR ® 825 |
| 27.55 | Colorants | 15.00 | |
| 0.20 | Germall 115 | | |
| 0.15 | Methylparaben | | |
| 0.10 | Propylparaben | | |
| 85.00 | | | |

Pressed samples were prepared using a "Carver", model 300 laboratory-style powder press. Each sample was pressed in the laboratory at 1157 psi into godets having the same configuration and dimensions of the godets used in Example 2.

EXAMPLE 9

An eight pound laboratory batch of an eye shadow formulation EMS-13-94 Batch (Rose-Lid) were prepared using the identical procedure as was used in preparing the formulation of Example 8. The formulation contained the following amounts (percent by weight) of ingredients:

| Dry Ingredients | | Liquid/Solid Ingredients | |
| --- | --- | --- | --- |
| 30.05 | Titanated Mica | 4.30 | Ceraphyl 368 |
| 30.00 | Colorants | 3.57 | Liponate PO-4 |
| 10.00 | Mica | 2.90 | Softisan 100 ® |
| 6.00 | Talc | 2.80 | Petroleum Jelly |
| 6.00 | Zinc Stearate | 1.43 | VYBAR ® 825 |
| 2.50 | SILTEK M | 15.00 | |
| 0.20 | Germall 115 | | |
| 0.15 | Methylparaben | | |
| 0.10 | Propylparaben | | |
| 85.00 | | | |

Pressed samples were prepared essentially in accordance with the procedure used in Example 1; however, each sample was pressed at 4908 psi into godets having the same configuration and dimensions of the godets used in Example 1 and the pressing speed was approximately 52 pieces per minute.

EXAMPLE 10

An eight pound laboratory batch of an eye shadow formulation MPG-03-82 (Light Blue) was prepared using the identical procedure as was used in preparing the formulation of Example 8. The formulation contained the following amounts (percent by weight) of ingredients:

| Dry Ingredients | | Liquid/Solid Ingredients | |
|---|---|---|---|
| 40.00 | Titanated Mica | 4.30 | Ceraphyl 368 |
| 20.00 | Mica | 3.57 | Liponate PO-4 |
| 20.00 | Bismuth Oxychloride | 2.90 | Softisan 100 ® |
| 5.00 | SILTEK M | 2.80 | Petroleum Jelly |
| 85.00 | | 1.43 | VYBAR ® 825 |
| | | 15.00 | |

Pressed samples were prepared essentially in accordance with the procedure used in Example 8; however, each sample was pressed in the laboratory at 1736 psi into godets having the same configuration and dimensions of the godets used in Example 2

EXAMPLE 11

An eight pound laboratory batch of an eye shadow formulation MPG-03-112 (Blue) was prepared using the identical procedure as was used in preparing the formulaton of Example 8. The formulation contained the following amounts (percent by weight) of ingredients:

| Dry Ingredients | | Liquid/Solid Ingredients | |
|---|---|---|---|
| 40.00 | Titanated Mica | 4.30 | Ceraphyl 368 |
| 40.00 | Talc | 3.57 | Liponate PO-4 |
| 5.00 | SILTEK M | 2.90 | Softisan 100 ® |
| 85.00 | | 2.80 | Petroleum Jelly |
| | | 1.43 | VYBAR ® 825 |
| | | 15.00 | |

Pressed samples were prepared essentially in accordance with the procedure used in Example 8; however, each sample was pressed in the laboratory at 1061 psi into godets having the same configuration and dimensions of the godets used in Example 2.

EXAMPLE 12

An eight pound laboratory batch of an eye shadow formulation MPG-03-104 (Celadon) was prepared using the identical procedure as was used in preparing the formulation of Example 8. The formulation contained the following amounts (percent by weight) of ingredients:

| Dry Ingredients | | Liquid/Solid Ingredients | |
|---|---|---|---|
| 32.00 | Titanated Mica | 4.30 | Ceraphyl 368 |
| 20.00 | Mica | 3.57 | Liponate PO-4 |
| 20.00 | Bismuth Oxychloride | 2.90 | Softisan 100 ® |
| 6.00 | Talc | 2.80 | Petroleum Jelly |
| 5.00 | SILTEK M | 1.43 | VYBAR ® 825 |
| 1.55 | Colorants | 15.00 | |
| 0.20 | Germall 115 | | |
| 0.15 | Methylparaben | | |
| 0.10 | Propylparaben | | |
| 85.00 | | | |

Pressed samples were prepared essentially in accordance with the procedure used in Example 8; however, each sample was pressed in the laboratory at 1446 psi into godets having the same configuration and dimensions of the godets used in Example 2.

EXAMPLE 13

An eight pound laboratory batch of an eye shadow formulation MPG-03-86 (Celadon) was prepared using the identical procedure as was used in preparing the formulation of Example 8. The formulation contained the following amounts (percent by weight) of ingredients:

| Dry Ingredients | | Liquid/Solid Ingredients | |
|---|---|---|---|
| 26.00 | Titanated Mica | 4.30 | Ceraphyl 368 |
| 20.00 | Mica | 3.57 | Liponate PO-4 |
| 20.00 | Bismuth Oxychloride | 2.90 | Softisan 100 ® |
| 6.00 | Talc | 2.80 | Petroleum Jelly |
| 6.00 | Lithium Stearate | 1.43 | VYBAR ® 825 |
| 5.00 | SILTEK M | 15.00 | |
| 1.55 | Colorants | | |
| 0.20 | Germall 115 | | |
| 0.15 | Methylparaben | | |
| 0.10 | Propylparaben | | |
| 85.00 | | | |

Pressed samples were prepared essentially in accordance with the procedure used in Example 8; however, each sample was pressed in the laboratory at 1639 psi into godets having the same configuration and dimensions of the godets used in Example 2.

EXAMPLE 14

An eight pound laboratory batch of an eye shadow formulation MPG-03-88 (Blue) was prepared using the identical procedured as was used in preparing the formulation of Example 8. The formulation contained the following amounts (percent by weight) of ingredients:

| Dry Ingredients | | Liquid/Solid Ingredients | |
|---|---|---|---|
| 26.50 | Titanated Mica | 4.30 | Isopropyl Palmitate |
| 20.00 | Mica | 3.57 | Liponate PO-4 |
| 20.00 | Bismuth Oxychloride | 2.90 | Softisan 100 ® |
| 6.00 | Talc | 2.80 | Petroleum Jelly |
| 6.00 | Zinc Stearate | 1.43 | VYBAR ®825 |
| 5.00 | SILTEK M | 15.00 | |
| 1.05 | Colorants | | |
| 0.20 | Germall 115 | | |
| 0.15 | Methylparaben | | |
| 0.10 | Propylparaben | | |
| 85.00 | | | |

Pressed samples were prepared essentially in accordance with the procedure used in Example 8; however, each sample was pressed in the laboratory at 1446 psi into godets having the same configuration and dimensions of the godets used in Example 2.

EXAMPLE 15

An eight pound laboratory batch of an eye shadow formulation MPG-03-90 (Blue) was prepared using the identical procedure as was used in preparing the formulation of Example 8. The formulation contained the following amounts (percent by weight) of ingredients:

| Dry Ingredients | | Liquid/Solid Ingredients | |
|---|---|---|---|
| 26.50 | Titanated Mica | 4.30 | Ceraphyl 368 |
| 20.00 | Mica | 3.57 | Liponate PO-4 |
| 20.00 | Bismuth Oxychloride | 2.90 | Caprylic/Capril/ Stearic Triglyceride |

| Dry Ingredients | | Liquid/Solid Ingredients | |
|---|---|---|---|
| 6.00 | Talc | 1.43 | VYBAR ® 825 |
| 6.00 | Zinc Stearate | 2.80 | Petroleum Jelly |
| 5.00 | SILTEK M | 15.00 | |
| 1.05 | Colorants | | |
| 0.20 | Germall 115 | | |
| 0.15 | Methylparaben | | |
| 0.10 | Propylparaben | | |
| 85.00 | | | |

Pressed samples were prepared essentially in accordance with the procedure used in Example 8; however, each sample was pressed in the laboratory at 1446 psi into godets having the same configuration and dimensions of the godets used in Example 2.

EXAMPLE 16

An eight pound laboratory batch of an eye shadow formulation MPG-03-116 (Peach) was prepared using the identical procedure as was used in preparing the formulation of Example 8. The formulation contained the following amounts (percent by weight) of ingredients:

| Dry Ingredients | | Liquid/Solid Ingredients | |
|---|---|---|---|
| 26.50 | Titanated Mica | 4.30 | Ceraphyl 368 |
| 20.00 | Mica | 3.57 | Pentarythrytol Tetra Isocaprylate |
| 20.00 | Bismuth Oxychloride | 2.90 | Softisan 100 ® |
| 6.00 | Talc | 2.80 | Petroleum Jelly |
| 6.00 | Zinc Stearate | 1.43 | VYBAR ® 825 |
| 5.00 | SILTEK M | 15.00 | |
| 1.05 | Colorants | | |
| 0.20 | Germall 115 | | |
| 0.15 | Methylparaben | | |
| 0.10 | Propylparaben | | |
| 85.00 | | | |

Pressed samples were prepared essentially in accordance with the procedure used in Example 8; however, each sample was pressed in the laboratory at 1446 psi into godets having the same configuration and dimensions of the godets used in Example 2.

EXAMPLE 17

An eight pound laboratory bach of an eye shadow formulation MPG-03-118 (Peach) was prepared using the identical procedure as was used in preparing the formulation of Example 8. The formulation contained the following amounts (percent by weight) of ingredients:

| Dry Ingredients | | Liquid/Solid Ingredients | |
|---|---|---|---|
| 36.55 | Titanated Mica | 6.87 | Liponate PO-4 |
| 20.00 | Mica | 5.38 | Petroleum Jelly |
| 10.00 | Bismuth Oxychloride | 2.75 | VYBAR ®825 |
| 6.00 | Talc | 15.00 | |
| 6.00 | Zinc Stearate | | |
| 5.00 | SILTEK M | | |
| 1.00 | Colorants | | |
| 0.20 | Germall 115 | | |
| 0.15 | Methylparaben | | |
| 0.10 | Propylparaben | | |
| 85.00 | | | |

Pressed samples were prepared essentially in accordance with the procedure used in Example 8; however, each sample was pressed in the laboratory at 1466 psi into godets having the same configuration and dimensions of the godets used in Example 2.

EXAMPLE 18

An eight pound laboratory batch of an eye shadow formulation MPG-03-136 was prepared using the identical procedure as was used in preparing the formulation of Example 8. The formulation contained the following amounts (percent by weight) of ingredients:

| Dry Ingredients | | Liquid/Solid Ingredients | |
|---|---|---|---|
| 36.55 | Titanated Mica | 6.87 | Liponate PO-4 |
| 20.00 | Mica | 5.38 | Petroleum Jelly |
| 10.00 | Bismuth Oxychloride | 2.75 | VYBAR ® 825 |
| 5.00 | SILTEK M | 15.00 | |
| 13.45 | Colorants | | |
| 85.00 | | | |

Pressed samples were prepared essentially in accordance with the procedure used in Example 8; however, each sample was pressed in the laboratory at 1466 psi into godets having the same configuration and dimensions of the godets used in Example 2.

EXAMPLE 19

An eight pound laboratory batch of an eye shadow formulation MPG-03-80 was prepared using the identical procedure as was used in preparing the formulation of Example 8. The formulation contained the following amounts (percent by weight) of ingredients:

| Dry Ingredients | | Liquid/Solid Ingredients | |
|---|---|---|---|
| 56.55 | Titanated Mica | 4.30 | Ceraphyl 368 |
| 10.00 | Bismuth Oxychloride | 3.75 | Liponate PO-4 |
| 6.00 | Talc | 2.90 | Softisan 100 ® |
| 6.00 | Zinc Stearate | 2.80 | Petroleum Jelly |
| 5.00 | SILTEK M | 1.43 | VYBAR ® 825 |
| 1.00 | Colorants | 15.00 | |
| 0.20 | Germall 115 | | |
| 0.15 | Methylparaben | | |
| 0.10 | Propylparaben | | |
| 85.00 | | | |

Pressed samples were prepared essentially in accordance with the procedure used in Example 8; however, each sample was pressed in the laboratory at 1446 psi into godets having the same configuration and dimensions of the godets used in Example 2.

EXAMPLE 20

An eight pound laboratory batch of an eye shadow formulation MPG-03-128 (Blue) was prepared using the identical procedure as was used in preparing the formulation of Example 8. The formulation contained the following amounts (percent by weight) of ingredients:

| Dry Ingredients | | Liquid/Solid Ingredients | |
|---|---|---|---|
| 36.50 | Titanated Mica | 4.30 | Isopropyl Palmitate |
| 20.00 | Mica | 3.57 | Pentarythrytol Tetra Isocaprylate |
| 10.00 | Bismuth Oxychloride | 2.90 | Caprylic/Capril/ Stearic Triglyceride |
| 6.00 | Talc | 2.80 | Petroleum Jelly |
| 6.00 | Zinc Stearate | 1.43 | VYBAR ® 825 |
| 5.00 | SILTEK M | 15.00 | |
| 1.05 | Colorants | | |
| 0.20 | Germall 115 | | |
| 0.15 | Methylparaben | | |

-continued

| Dry Ingredients | Liquid/Solid Ingredients |
|---|---|
| 0.10 Propylparaben | |
| 85.00 | |

Pressed samples were prepared essentially in accordance with the procedure used in Example 8; however, each sample was pressed in the laboratory at 1061 psi into godets having the same configuration and dimensions of the godets used in Example 2.

Each of the sets of pressed powder eye shadow samples prepared in Examples 1 through 20 were evaluated using standard industry criteria—Drop Test, Penetration and Application. The results of the evaluation are presented below in Table III.

TABLE III

| Examples | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Drop Test (1) | 0/10 | 0/10 | 0/10 | 4/10 | 0/10 | 2/10 | 0/10 | 0/10 | 0/1 | 0/10 | 0/10 | 0/10 | 0/10 | 0/10 |
| Penetration (2) | 12/15 | 10/15 | 15/19 | 20/25 | 6/15 | 18/23 | 13/18 | 12/17 | 7/1 | 15/19 | 10/15 | 14/20 | 14/18 | 13/19 |
| Application (3) | * | * | * | * | * | * | * | * | * | * | * | * | * | * |

| Examples | 15 | 16 | 17 | 18 | 19 | 20 |
|---|---|---|---|---|---|---|
| Drop Test (1) | 0/10 | 1/10 | 0/10 | 0/10 | 0/10 | 0/10 |
| Penetration (2) | 12/18 | 17/25 | 16/24 | 15.20 | 15/20 | 15/20 |
| Application (3) | * | * | * | * | * | * |

(1) Drop Test - Drop a total of ten godets from a distance of 24 inches onto a ⅛ inch rubber tile over a concrete floor. Make sure that all the godets dropped land in an upright position. Any godets landing on their sides or front should be discarded and not counted. A failure is indicated if one out of ten samples fractures.
(2) Penetration - Test a total of five godets. Measure in center of cake. Use small brass cone, (weight 47.5 grams). Do not use any weight on rod. The purpose of the test is to measure the cake hardness. The respective figures are .1 mm. Acceptable range is between about 6 and 25.
(3) Application - Rub the surface of the sample and the control with a clean sponge applicator. The sample should equal the control in application with no glazing or flaking. Application should be the same along both lengthwise edges. Two samples should be tested. Acceptable results are indicated by an asterik (*).

Thereafter, each of the production batches of pressed powder eye shadow samples prepared in Examples 1 through 7 were assembled into compacts and packaged carded and uncarded into packages of three. A protective divider (compact scuffing) was added as is done with all current uncarded compacts. Packages were then assembled into master cartons of 72 pieces. Each master carton was then subjected to the standard industry "ship test" which entailed vibrating the top, bottom, and side of each master carton for twenty minutes (total one hour) and thereafter dropping each master carton six times, once on each side, from a height of three feet. This test is standard for UPS requirements for packages weighing less than fifteen pounds (National Safe Transit Association Pre-Shipment Test Procedure Project 1A).

The results of the "ship test" are set out below in Table IV.

TABLE IV

| Example No. | Results |
|---|---|
| #1 | Passed - no breakage |
| #2 | Passed - no breakage |
| #3 | Passed - no breakage |
| #4 | Failed |
| #5 | Passed - no breakage |
| #6 | Failed |
| #7 | Passed - no breakage |

The pressed powder eye shadow composition produced in accordance with the present invention can be easily applied to the skin to provide a lustrous adherent color film with excellent wear properties and dramatic pearlescent affects. The aforesaid compositions are further characterized by the ability to formulate the same with acceptable compatibility at maximum operating speeds and in receptacles having a wide variety of shapes and sizes, particularly in godets having large dimensions.

I claim:

1. A pressed powder cosmetic composition containing a binder and from about 40 to about 80% by weight of nacreous material, said binder comprising a dry binder ingredient consisting of a cosmetically suitable micronized polyethylene wax and a mixture of liquid/solid binder ingredients comprising petrolatum; a cosmetically suitable tetraester having the formula

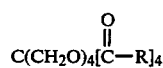

wherein R may be a straight, branched, saturated or unsaturated alkyl having from 5 to 21 carbon atoms; and a cosmetically suitable polyolefin formed by polymerizing an alphaolefin having the formula $RCH=CH_2$, wherein R is a hydrocarbon group having from 3 to 18 carbon atoms.

2. A composition according to claim 1, wherein the nacreous material is selected from the group consisting of natural pearl, mica, bismuth oxychloride, bismuth oxychloride on mica, titanated mica, and titanated mica and iron oxide.

3. A composition according to claim 2 wherein the amount of nacreous material is present in an amount ranging from about 45% by weight to about 70% by weight.

4. A composition according to claim 1 wherein the dry binder ingredient is a micronized polyethylene wax having a molecular weight range from about 600 to about 4000 and having a particle size from about 2 microns to 35 microns, said ingredient being present in an amount ranging from about 0.1% to about 15% by weight.

5. A composition according to claim 4 wherein the molecular weight of the micronized polyethylene wax ranges from about 700 to about 800.

6. A composition according to claim 4 wherein the micronized polyethylene wax is present in an amount ranging from about 0.5% to about 9% by weight.

7. A composition according to claim 1 wherein the petrolatum ingredient in the binder mixture is present in an amount ranging from about 0.25 to about 5.5% by weight.

8. A composition according to claim 7 wherein the petrolatum is present in an amount ranging from 0.75% to about 3.5% by weight.

9. A composition according to claim 1 wherein the tetraester ingredient is a tetraester of pentaerythritol and a cosmetically suitable acid selected from the grop coonsisting of lauric, oleic, stearic, palmitic, linoleic, isostearic, hydroxystearic, acetic and branched chain nonanoic acid.

10. A composition according to claim 9 wherein the tetraester is present in an amount ranging from about 1.0% to about 15.0% by weight.

11. A composition according to claim 9 wherein the tetraester is a tetraester of pentaerythritol and oleic acid.

12. A composition according to claim 1 wherein the polyolefin ingredient is selected from the group consisting of hexene-1, heptene-1, octene-1, decene-1, undecene-1, dodecene-1 and tetradecene-1.

13. A composition according to claim 12 wherein the polyolefin ingredient is present in an amount ranging from about 0.1% to about 3% by weight.

14. A composition according to claim 12 wherein the polyolefin is VYBAR ®825.

15. A composition according to claim 1 containing talc, metal soap, colorant, fragrance and preservative and wherein the talc is a filler selected from the group consisting of transparent talcs and is present in amounts up to about 40% by weight; the metal soap is selected from the group consisting of zinc, lithium, magnesium and calcium stearates and is present in amounts up to aout 6% by weight; the colorant is selected from inorganic and natural pigments and is present in amounts up to about 30.0% by weight; the fragrance is a cosmetically acceptable fragrance and is present in a fragrance-effective amount; and the preservatives are selected from cosmetically acceptable preservatives.

16. A composition according to claim 1 wherein the binder mixture contains a fatty ester having the formula

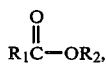

wherein $R_1$ is a group containing from 1 to 21 carbon atoms which may be straight or branched, saturated or unsaturated and which may contain hydroxyl groups; $R_2$ is a group containing from 1 to 22 carbon atoms which may be straight, branched, saturated or unsaturated and which may contain hydroxyl groups; and wherein $R_1$ and $R_2$ may be the same or different; or the formula

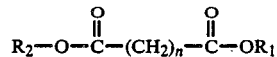

wherein n is an integer from 2 to 6 and $R_1$ and $R_2$ have the same meanings as above and may be the same or different.

17. A composition according to claim 16 wherein the fatty ester is present in amounts up to about 15.0% by weight.

18. A composition according to claim 16 wherein the fatty ester is selected from the group consisting of octyl palmitate, isopropyl palmitate, isostearyl neopentanoate, isopropyl lanolate and isopropyl myristate.

19. A composition according to claim 1 wherein the binder mixture contains a triester of glycerine and a cosmetically suitable acid selected from the group consisting of lauric, stearic, oleic, palmitic, linoleic, isostearic, hydroxystearic, acetic branched chain nonanioc acid.

20. A composition according to claim 19 wherein the triester ingredient is trilaurin.

21. A composition according to claim 19 wherein the triester is present in an amount up to about 7.0% by weight.

22. A composition according to claim 9 wherein the tetraester is present in an amount ranging from about 2.0% to about 4.5% by weight.

23. A composition according to claim 12 wherein the polyolefin ingredient is present in an amount ranging from about 0.5% to about 2% by weight.

24. A composition according to claim 16 wherein the fatty acid is present in amounts ranging from about 1.5% to about 5.5% by weight.

25. A composition according to claim 19 wherein the triester is present in an amount ranging from about 0.4% to about 5.5% by weight.

* * * * *

UNITED STATES PATENT AND TRADEMARK OFFICE
CERTIFICATE OF CORRECTION

PATENT NO. : 4,534,963
DATED : August 13, 1985
INVENTOR(S) : Philip J. Gordon

It is certified that error appears in the above-identified patent and that said Letters Patent is hereby corrected as shown below:

Column 1, line 67, after "satisfactory" insert --compaction--;
Column 4, line 3, "Petroleum" should read --Petrolatum--;
Column 4, line 32, "the U.S." should read --in U.S.--;
Column 5, line 39, delete the comma after "isopropyl";
Column 6, line 68, "was prepared" should read --were prepared--;
Column 10, line 34, "procedured" should read --procedure--;
Column 12, line 28, "MPG-03-80" should read --MPG-03-126--;
Column 13, TABLE III, Drop Test (1), Example 9, "0/1" should read --0/10--;
Column 13, TABLE III, Penetration (2), Example 9, "7/1" should read --7/10--; and
Column, 13, last line of footnotes to TABLE III, "asterik" should read --asterisk--; and
Column 15, lines 8 and 9, "grop coonsisting" should read --group consisting--.

Signed and Sealed this

Twenty-eighth Day of October, 1986

[SEAL]

Attest:

DONALD J. QUIGG

Attesting Officer     Commissioner of Patents and Trademarks